United States Patent
De Oliveria Barroso Júnior

(10) Patent No.: US 8,972,014 B2
(45) Date of Patent: Mar. 3, 2015

(54) ENURESIS ELECTROCONDITIONER

(76) Inventor: Ubirajara De Oliveria Barroso Júnior, Salvador/BA (BR)

(*) Notice: Subject to any disclaimer, the term of this patent is extended or adjusted under 35 U.S.C. 154(b) by 169 days.

(21) Appl. No.: 13/634,709

(22) PCT Filed: Feb. 14, 2011

(86) PCT No.: PCT/BR2011/000052
§ 371 (c)(1),
(2), (4) Date: Sep. 13, 2012

(87) PCT Pub. No.: WO2011/113122
PCT Pub. Date: Sep. 22, 2011

(65) Prior Publication Data
US 2013/0013022 A1    Jan. 10, 2013

(30) Foreign Application Priority Data
Mar. 19, 2010    (BR) ................. PI1000674-5

(51) Int. Cl.
*A61N 1/00*    (2006.01)
*A61F 5/48*    (2006.01)
*A61N 1/36*    (2006.01)

(52) U.S. Cl.
CPC .............. *A61F 5/48* (2013.01); *A61N 1/36007* (2013.01)
USPC .................. 607/41; 607/40; 607/58

(58) Field of Classification Search
CPC .................................. A61N 1/36007
USPC ................................ 607/40, 41, 58
See application file for complete search history.

(56) References Cited

U.S. PATENT DOCUMENTS

| | | | | |
|---|---|---|---|---|
| 5,036,859 A | * | 8/1991 | Brown | 600/547 |
| 5,562,717 A | * | 10/1996 | Tippey et al. | 607/41 |
| 5,573,552 A | | 11/1996 | Hansjurgens | |
| 8,000,792 B1 | * | 8/2011 | Dechev et al. | 607/41 |

FOREIGN PATENT DOCUMENTS

| | | |
|---|---|---|
| CN | 86207621 U | 12/1988 |
| CN | 2054687 U | 3/1990 |
| CN | 1088122 A | 6/1994 |
| CN | 1208658 A | 2/1999 |
| CN | 2907737 Y | 6/2007 |
| FR | 2057567 A5 | 5/1971 |
| FR | 2347942 A1 | 11/1977 |
| FR | 2611506 A | 9/1988 |
| UA | 74829 C2 | 7/2004 |
| UA | 80419 C2 | 9/2007 |

OTHER PUBLICATIONS

Microchip Tecnologies Inc., PIC16F62X Data Sheet Flash-Based 8-Bit CMOS Microcontroller, 2003.

* cited by examiner

*Primary Examiner* — Michael Kahelin
*Assistant Examiner* — Mallika D Fairchild
(74) *Attorney, Agent, or Firm* — Richard M. Goldberg

(57) ABSTRACT

An enuresis electroconditioner pertains to the field of medical appliances and includes a humidity sensor (2) connected to an electric circuit which is activated in the presence of a liquid. When the liquid is detected, an electric current with a frequency of 50 Hz is generated. A qualified person must calibrate the amperage of the apparatus (1), adapting it to the sensibility of each person who, when receiving the electric impulse, contracts the perineal muscles, occluding the urethra and by a reflexive action inhibiting the contraction of the bladder and preventing urine loss.

12 Claims, 2 Drawing Sheets

ENURESIS ELECTROCONDITIONER

BACKGROUND OF THE INVENTION

This invention is a device which was developed to treat nocturnal enuresis and belongs to the scope of the medical devices industry.

Currently, nocturnal enuresis is treated with medication or with the use of an enuresis alarm, the latter being the best long-term treatment. This is because this unit trains the person to inhibit bladder contraction during the sleep, producing a lasting result. Although this treatment is well-established and used around the world, several problems prevent many individuals from obtaining therapeutic success. These include those who usually take weeks to train their reactions, and during this period, remain urinating in bed, which leads many to give up the method. Besides, other family members wake up because of the alarm, resulting in emotional distress and family conflicts.

SUMMARY OF THE INVENTION

The purpose of this invention is to continue with the benefits of the enuresis alarm conditioning principle, but preventing the aforementioned problems.

This invention consists of a humidity sensor, similar to those which already exist, which is connected to an electrical circuit that is activated when the sensor is stimulated by moisture. From that, an electric current with 50 Hz frequency is generated.

The amperage of the device must be previously calibrated by a professional, since it must not exceed the sensitivity threshold that is different for every individual. With this current frequency, they tighten the perineal muscles, occluding the urethra, inhibiting reflex bladder contraction, thus preventing urination. The electrodes that will send the electrical current to the skin will be superficial and placed in the perianal area.

The research conducted at the INPI (acronym, in Portuguese, for the Brazilian National Institute of Industrial Property) received the registration nr. 0041/10 and pointed out several particularly relevant processes, in what concerns the researcher. The inventor himself analyzed it carefully and came to the conclusion that the patented invention does not resemble any of the devices presented by the search. The purpose of this invention, unlike all presented devices, is to, after stimulation of the humidity sensor as a result of nocturnal urination, have an electrical stimulation of the perineal muscles' innervations, causing a contraction of the external urethral sphincter. This contraction will cause urine flow to stop immediately, preventing nocturnal urination. Unlike other devices, the "Enuresis Electroconditioner" uses a current with a 50 Hz frequency, which is the most appropriate for stopping urination. Currents with frequencies lower than 30 Hz, such as those presented by other patents, do not contract the muscles.

After a few episodes of activation of the device, the person grows trained and gains control of nocturnal urination.

This invention will present a sound alarm as an option, but fundamentally, this is not the principle. The humidity sensor is not just to warn the person that they are urinating, but to activate the electrical stimulator, so urination may stop. In the cases mentioned during the survey as particularly relevant, the ones with the registration numbers CN 1088122 A and CN 1208658 A, an abdominal nerve is stimulated so as to make the brain learn and cure incontinence. No device was designed, based on the stimulation of the perineal muscles, so as to immediately stop urine flow during an episode of nocturnal enuresis. Therefore, the idea is innovative. Over time, the training starts to show and the person himself (herself), unconsciously, controls urination during sleep. This treatment is way ahead of all currently used devices, because it prevents nocturnal incontinence while the brain is being trained.

In patent CN 1208658, a regular stimulation, with a preset schedule, is used, and it is not activated in accordance with the humidity sensor, like this device.

In patent CN 86207621, the device does not have the Enuresis Electroconditioner's operating principles (humidity sensor and perineal electrical stimulation), besides having a variable current frequency from 1 to 15 HZ, while in this, frequency is set at 10 Hz.

In patent CN 2907737Y, stimulation is applied on the penis and on the clitoris, and the operating principles differ from the ones applied in the "Enuresis Electroconditioner". X In patent UA 74829, electrical stimulation is executed with compresses placed on the bed, around the hip of the person, and the current frequency is 30 Hz. Therefore, it differs completely from the object of this patent application.

BRIEF DESCRIPTION OF THE DRAWINGS

In order to better understand the operation of this device, refer to the attached drawings.

As can be seen on the drawings.

DETAILED DESCRIPTION

Figure 1:
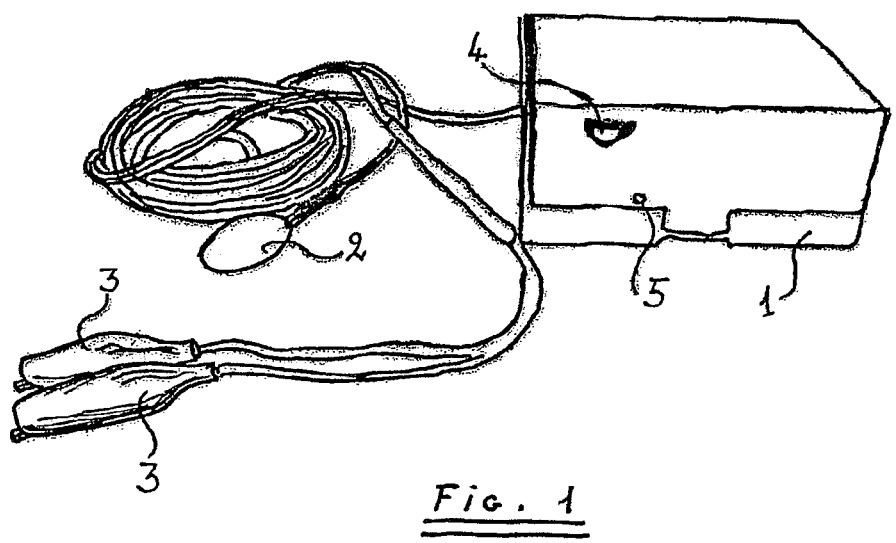
FIG. 1 is an external view of the apparatus.
Figure 2:
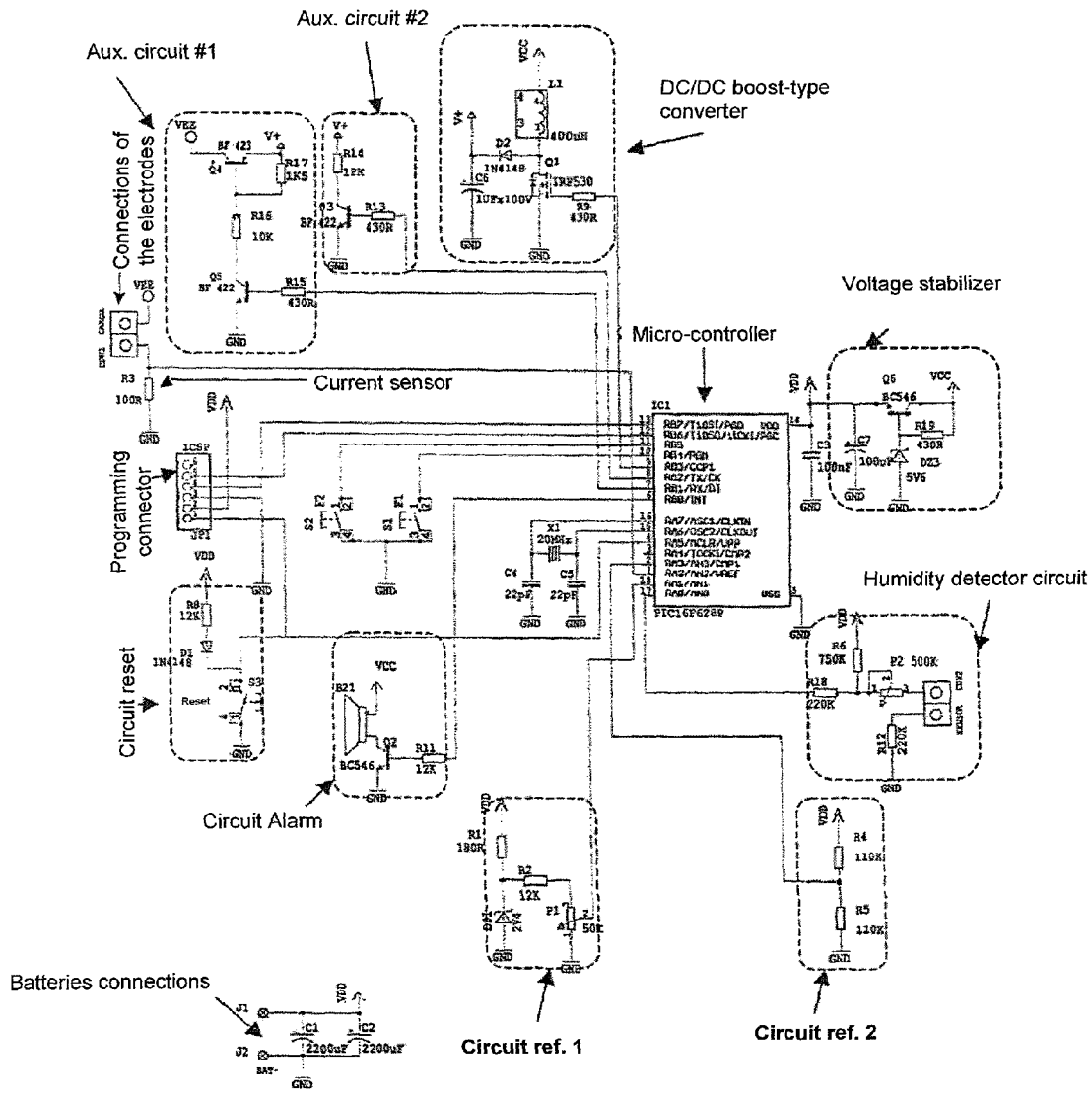
FIG. 2 depicts the operating electronic scheme.

The enuresis electroconditioner is made up of a portable electronic device (1) capable of detecting the presence of urine with a specifically designed humidity sensor (2), and generating a unidirectional, square-wave-shaped electrical signal, with 50 (fifty) Hz frequency and pulse width of 700 microseconds, with adjustable current intensity from 0 mA (zero milliamps) to approximately 35 mA (thirty-five milliamps), depending on the impedance of the area to be electrically stimulated. In the areas which will be electrically stimulated, the electrodes which will be connected to the clamps (3) will be applied.

The portable electronic device (1) is powered by batteries, depending on the model. The device can be turned on with the on/off switch (4) (or any other suitable means) and has a lit LED display (5).

Operational Mode

The Normal Operating Mode (MON) is the default operating mode of the device. Whenever it is turned on, MON will be automatically selected. In this mode, the device monitors the humidity sensor (2) so as to detect the presence of electricity-conducting liquids (urine, sweat, saliva, potable water, etc.). If the sensor (2) is not activated, no electrical signal is sent to the clamps (3) and no sound is emitted by the alarm. When a certain amount of electricity-conducting liquid (urine, in this case) touches the sensor, depending on the sensitivity setting, the unit (1) starts sending, for a few seconds, an electrical signal according to the technical specifications and with an intensity equal to the one which was previously set.

Description of the Circuit Stages

Boost Converter

The circuit formed by Q1, D2, L1 and C6 configures a "Boost-type DC/DC Converter" where Q1 is the switching element and the output voltage adjustment (V+) is performed by the PWM-type control circuit which is built-in in the PIC. The PIC's pin 9 (CCP1) operates as a PWM outlet, switching at 50 KHz with a variable duty cycle.

Aux. Circuit 2

The "DC/DC Converter" takes approximately 200 microseconds to establish an output voltage. The "Aux. Circuit 2" is activated during this converter stabilization time, placing a temporary load (R14) on the converter outlet, so that it does not remain open during stabilization time.

Aux. Circuit 1

This circuit operates as an electronic switch, allowing the current to pass to the load (electrodes) for the duration of 700 microseconds during the electrical stimulation cycle, since the "DC/DC Converter" must be turned on 200 microseconds before, in order to wait for stabilization.

"Current Sensor" and "Circuit Ref. 1"

These two circuits operate in pairs as inputs to a comparator circuit within the microcontroller. R3 is in series with the load (electrodes) and operates as a shunt resistor. "The Circuit ref. 1", via P1 setting, provides a reference voltage for the comparator. When the Electroconditioner is in the high time of the electrical stimulation stage (sending current to the electrodes), the Microcontroller adjusts the PWM circuit's duty cycle to increase or decrease the output voltage (V+) of the "DC/DC Converter", so as to obtain, on the load, the previously adjusted current through P1.

Circuit Reset

Resets the Microcontroller whenever S3 is activated.

Circuit Alarm

A sound signal whenever it receives a signal from the Microcontroller.

Circuit Ref. 2 and Humidity Detector

These two circuits operate in pairs as inputs to a comparator circuit within the Microcontroller. Whenever there is, in the sensor (pair of conductors), an impedance which is lower than a value that can vary from 30 to 530 Kohms, depending on the P2 setting, the Microcontroller understands that the sensor is wet and activates the electrical stimulation mode.

Voltage Stabilizer

This circuit maintains a stable voltage on the Microcontroller and on the reference circuits, even when there is some variation on the charging of the batteries.

Description of Overall Operation

After it is turned on, the unit automatically enters the normal operating mode (MON), i.e., the Microcontroller starts to monitor the humidity detector, and remains so until it is switched off or adjusted to the set mode (MA).

When liquid is detected, the Microcontroller starts turning the "DC/DC Converter" on and off with a 50 Hz frequency for the duration of 900 microseconds, and the first 200 microseconds of this cycle are only to ensure output voltage stability, and only then, voltage is sent to the load, when turning the Aux. Circuit 2 on.

During the 700 microseconds in which output voltage is being applied to the load, the Microcontroller monitors the voltage on the shunt resistor (R3) with the voltage set on "Circuit ref. 2". While voltage on R3 is lower than the set voltage, the PWM output's duty cycle is increased in order to increase the load voltage and reach the set current. The output voltage always starts from the lowest possible (battery voltage) and increases until voltage on R3 is the same set voltage in "Circuit ref. 2".

If voltage on R3 exceeds the adjusted voltage in "Circuit ref. 2", the PWM's duty cycle is decreased so that the output voltage of the "DC/DC Converter" is also decreased.

During this process, if the output voltage reaches a maximum (approximately 80 volts with fully charged batteries), and the load current does not reach the value set in "Circuit ref. 2", the device emits an intermittent sound with short and quick beeps.

The control described above takes place in a few nanoseconds. The effect of this process is the maintenance of a square-wave-shaped current and a 50 Hz frequency with constant intensity during the high time of 700 microseconds.

Twenty seconds after liquid is detected by the humidity sensor, the output current is automatically switched off and the unit emits an intermittent sound alarm with long beeps in order to awaken the person so they may urinate.

What is claimed is:

1. Enuresis electroconditioner, comprising a portable electronic device including:
   a detector for detecting the presence of urine, the detector including a humidity sensor, and
   a stimulator for electrically stimulating an area of a person's body in response to the detection of the presence of urine by said detector to prevent further urination by the person by generation by the stimulator of a unidirectional, square-wave-shaped electrical signal, with a 50 Hz frequency and a pulse width of 700 microseconds, and with an adjustable current intensity from 0 mA to approximately 35 mA, depending on a previously determined impedance of the area to be electrically stimulated,
   wherein the portable electronic device includes:
      a DC/DC converter,
      an auxiliary circuit having an outlet,
      a reference circuit,
      a load,
      a shunt resistor, and
      a microcontroller which, when liquid is detected by the humidity sensor, starts turning the DC/DC Converter on and off with a 50 Hz frequency for a duration of 900 microseconds, with the first 200 microseconds of this 900 microseconds duration being provided only to ensure output voltage stability, and only after this first 200 microseconds duration, voltage is sent to the load, turning on the auxiliary circuit, and during the 700 microseconds duration in which output voltage is being applied to the load, the microcontroller monitors the voltage on the shunt resistor with a voltage set on the reference circuit, wherein when voltage on the shunt resistor is lower than the set voltage, the pulse width modulated duty cycle of the square-wave-shaped electrical signal is increased in order to increase the load voltage and reach a set current, with output voltage always starting from a lowest possible battery voltage and increasing until voltage on the shunt resistor is the same set voltage in as in the reference circuit, and if voltage on the shunt resistor exceeds the adjusted voltage in the reference circuit, the pulse width modulated duty cycle is decreased so that the output voltage of the DC/DC Converter is also decreased.

2. Enuresis electroconditioner in accordance with claim 1, further comprising two surface electrodes and clamps that are adapted to be connected to two surface electrodes wherein the electrodes are adapted to be placed on the buttocks of the person, on each side of the anus of the person, and electrically connected with said portable electronic device.

3. Enuresis electroconditioner in accordance with claim 2, further comprising an alarm, and wherein the portable electronic device does not send an electrical signal to the clamps and does not activate the alarm so that no sound is emitted by the alarm, when the humidity sensor is not activated.

4. Enuresis electroconditioner in accordance with claim 1, wherein the stimulator is configured to send an electrical signal to the area of the person's body during a few seconds, when a certain amount of urine touches the humidity sensor.

5. Enuresis electroconditioner in accordance with claim 1, wherein the microcontroller includes a pulse width modulation type control circuit and the DC/DC converter includes a switching element and an output voltage adjustment of the DC/DC converter is performed by the pulse width modulation type control circuit, switching at 50 KHz with a variable duty cycle.

6. Enuresis electroconditioner in accordance with claim 1, wherein the auxiliary circuit is activated during a stabilization period of the DC/DC converter, placing a temporary load at the outlet of the auxiliary circuit, during the stabilization period.

7. Enuresis electroconditioner in accordance with claim 1, wherein the portable electronic device includes a second auxiliary circuit which operates as an electronic switch, configured to allow current to pass to a load formed by electrodes placed on buttocks of the person for the duration of 700 microseconds during an electrical stimulation cycle, since the DC/DC converter must be turned on 200 microseconds before this electrical stimulation cycle, in order to wait for stabilization.

8. Enuresis electroconditioner in accordance with claim 1, wherein
the microcontroller includes a comparator circuit,
the portable electronic device further includes a current sensor and a second reference circuit which operate in pairs as inputs to the comparator circuit within the microcontroller, with the second reference circuit providing a reference voltage to the comparator, and
the portable electronic device includes the shunt resistor in series with the load formed by electrodes adapted to be placed on buttocks of the person,
wherein when the electroconditioner is in a high time of an electrical stimulation stage, sending current to the electrodes, the microcontroller adjusts the pulse width modulated duty cycle to increase or decrease the output voltage of the DC/DC Converter, so as to obtain, on the load, a previously adjusted current.

9. Enuresis electroconditioner in accordance with claim 1, wherein the portable electronic device includes a reset circuit having a reset switch and which resets the microcontroller whenever the reset switch in the reset circuit is activated.

10. Enuresis electroconditioner in accordance with claim 1, wherein the portable electronic device includes a circuit alarm which emits a sound signal whenever it receives a signal from the microcontroller.

11. Enuresis electroconditioner in accordance with claim 1, wherein the reference circuit and the humidity sensor operate in pairs as inputs to a comparator circuit within the microcontroller, wherein, whenever there is, in the humidity sensor, an impedance which is lower than a value that can vary from 30 to 530 Kohms, depending on a setting of the humidity sensor in the microcontroller, the microcontroller determines that the sensor is wet and activates an electrical stimulation mode.

12. Enuresis electroconditioner in accordance with claim 1, wherein the portable electronic device further includes a voltage stabilizer which maintains a stable voltage on the microcontroller and on the reference circuit, even when there is some variation on charging of batteries adapted to supply power to the portable electronic device.

* * * * *